United States Patent

Bormann et al.

[11] 4,120,965
[45] Oct. 17, 1978

[54] OCTAHYDRO-1,4-DIAZEPINO[1,7-b]ISOQUINOLINES

[75] Inventors: Gerhard Bormann, Munchenstein; Richard Berthold, Bottmingen, both of Switzerland

[73] Assignee: Sandoz Ltd., Basel, Switzerland

[21] Appl. No.: 798,314

[22] Filed: May 19, 1977

Related U.S. Application Data

[63] Continuation-in-part of Ser. No. 744,705, Nov. 24, 1976, abandoned, which is a continuation-in-part of Ser. No. 639,945, Dec. 11, 1975, abandoned.

[30] Foreign Application Priority Data

Dec. 20, 1974 [CH] Switzerland ............... 17020/74
May 19, 1976 [CH] Switzerland ............... 6255/76

[51] Int. Cl.² .................. C07D 471/04; A61K 31/47
[52] U.S. Cl. ............................. 424/258; 260/288 CF
[58] Field of Search .................. 260/288 CF; 424/258

[56] References Cited

U.S. PATENT DOCUMENTS

| 3,654,281 | 4/1972 | Montzka et al. | 260/288 CF |
| 3,853,851 | 12/1974 | Gschwend | 260/288 CF |
| 3,987,047 | 10/1976 | Griss et al. | 260/288 CF |

FOREIGN PATENT DOCUMENTS 2,555,532  7/1976  Fed. Rep. of Germany .......... 424/258

OTHER PUBLICATIONS

Bormann et al., Chem. Abs. vol. 85: 160186y (1976).
Geigy, Chem. Abs. vol. 64: 6664g (1966).

*Primary Examiner*—Donald G. Daus
*Assistant Examiner*—Mary C. Vaughn
*Attorney, Agent, or Firm*—Gerald D. Sharkin; Robert S. Honor; Timothy G. Rothwell

[57] ABSTRACT

This invention provides new compounds of formula I,

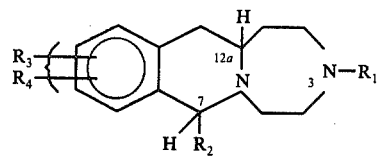

wherein
$R_1$ is hydrogen or alkyl of 1 to 5 carbon atoms,
$R_2$ is a group

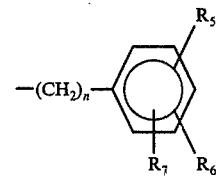

wherein
$n$ is a whole number from 0 to 3,
$R_5$ and $R_6$, independently, are hydrogen, alkyl of 1 to 4 carbon atoms, alkoxy of 1 to 4 carbon atoms, halogen of atomic number from 9 to 35, or together are 3,4-methylenedioxy,
$R_7$ is hydrogen, or when both $R_5$ and $R_6$ are alkoxy of 1 to 4 carbon atoms also may be alkoxy of 1 to 4 carbon atoms,
$R_3$ is hydrogen, alkyl of 1 to 4 carbon atoms, alkoxy of 1 to 4 carbon atoms, or halogen of atomic number from 9 to 35, and
$R_4$ is hydrogen or alkoxy of 1 to 4 carbon atoms, useful as sleep-promoting agents, and anti-aggressive agents.

57 Claims, No Drawings

OCTAHYDRO-1,4-DIAZEPINO[1,7-B]ISOQUINO-LINES

This application is a continuation-in-part of our co-pending application Ser. No. 744,705 filed Nov. 24, 1976 now abandoned, which in turn is a continuation-in-part of our copending application Ser. No. 639,945 filed Dec. 11, 1975 now abandoned.

The invention relates to octahydro-1,4-diazepino[1,7-b]isoquinolines.

The present invention provides compounds of formula I,

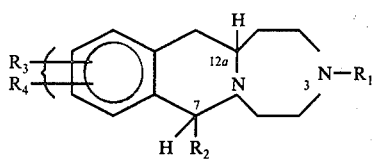

wherein
$R_1$ is hydrogen or alkyl of 1 to 5 carbon atoms,
$R_2$ is a group

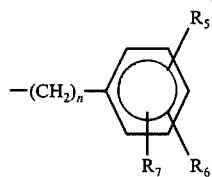

wherein
n is a whole number from 0 to 3,
$R_5$ and $R_6$, independently, are hydrogen, alkyl of 1 to 4 carbon atoms, alkoxy of 1 to 4 carbon atoms, halogen of atomic number from 9 to 35, or together are 3,4-methylenedioxy,
$R^7$ is hydrogen, or when both $R_5$ and $R^6$ are alkoxy of 1 to 4 carbon atoms also may be alkoxy of 1 to 4 carbon atoms,
$R_3$ is hydrogen, alkyl of 1 to 4 carbon atoms, alkoxy of 1 to 4 carbon atoms, or halogen of atomic number from 9 to 35, and
$R_4$ is hydrogen or alkoxy of 1 to 4 carbon atoms.

The configuration of the hydrogen atoms in the 7 and 12a positions of the 1,2,3,4,5,7,12,12a-octahydro-1,4-diazepino[1,7-b]isoquinoline residue may be cis (7RS,12aRS) or trans (7RS,12aSR).

Preferably $R_1$ is alkyl. Preferably $R_5$ and $R^6$ are hydrogen, halogen or alkoxy. Especially $R_6$ is hydrogen and $R_5$ is in the p-position.

$R_3$ and $R_4$ are in the 9 or 10-position of the tricyclic moiety and preferably are both hydrogen, or alkoxy, especially hydrogen.

Halogen is preferably chlorine. The alkyl and alkoxy moieties preferably have 1 or 2 carbon atoms. n is preferably 0 or 1.

The invention also provides a process for the production of a compound of formula I, as defined above, which comprises reducing a compound of formula II,

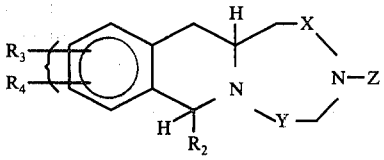

wherein
$R_2$, $R_3$ and $R_4$ are as defined above, and either
X is carbonyl,
Y is carbonyl or methylene, and
Z is the same as $R_1$, as defined above, or X and Y are methylene and
Z is alkanoyl of 1 to 5 carbon atoms, or alkoxycarbonyl of 2 to 5 carbon atoms in the aggregate thereof.

Y is preferably methylene. When $R_1$ is methyl, Z is preferably alkoxycarbonyl, especially ethoxycarbonyl, or methyl. When $R_1$ has more than 1 carbon atom, X is preferably carbonyl.

The process may be carried out in conventional manner for such reductions, e.g. under known conditions for the reduction of an N-substituted amide to the corresponding secondary or tertiary amine.

As reducing agents may be used metal hydrides, such as aluminium hydride, dialkylaluminium hydride or complex hydrides, especially complex aluminium hydrides such as lithium aluminium hydride, lithium aluminium hydride/aluminium chloride or disodium (2-methoxyethoxy) aluminium hydride in an inert solvent. When complex aluminium hydrides are used chlorine or bromine substituents may be replaced by hydrogen. Disodium (2-methoxyethoxy) aluminium hydride is especially preferred for the reduction of an alkoxycarbonyl group.

Generally it is convenient to use 1 to 4 moles of reducing agent per mole of compound of formula II.

The reaction temperature can vary between room temperature and 100° C., bearing in mind the type of substituents present. For the reduction of an alkoxycarbonyl group the reflux temperature is conveniently used.

The compounds of formula II are new, and may be produced according to known methods for the production of N-substituted amides and urethanes, e.g. from the corresponding γ-phenylacetoacetic acid ethyl ester.

Insofar as the production of any starting material is not particularly described these compounds are known, or may be produced and purified in accordance with known processes, or in a manner analogous to processes described herein, e.g. in the Examples; or to known processes.

Free base forms of compounds of formula I may be converted into acid addition salt forms in conventional manner and vice versa. Suitable acids for salt formation include hydrochloric acid, maleic acid, fumaric acid.

In the following Examples all temperatures are in degrees Centigrade and are uncorrected.

EXAMPLE 1:
(7RS,12aRS)-7-p-methoxyphenyl-3-methyl-1,2,3,4,5,7,12,12a-octahydro-1,4-diazepino-[1,7-b]isoquinoline 1.41 g of lithium aluminium hydride was added in portions to a solution of 12.5 g of (7RS,12aRS)-1,4,5,7,12,12a-hexahydro-7-p-methoxyphenyl-3-methyl-1,4-diazepino[1,7-b]isoquinolin-2(3H)-one in 210 ml of tetrahydrofuran. The temperature rose to about 50° C. The reaction mixture was refluxed for 30 minutes, stirred for another 2 hours and then to this mixture was added carefully dropwise 10 ml of methanol and 15 ml of a saturated solution of sodium sulphate. The resultant precipitate was filtered off. The filtrate was concentrated to dryness to afford the title compound (M.P. of the maleate from methanol/ether - 163° - 164°).

The starting material was obtained as follows:

(a) γ-Phenylacetoacetic acid ethyl ester was converted into 3-amino-4-phenylbutyric acid ethyl ester (M.P. of hydrogen oxalate 151°–153°). Further reaction with p-anisolyl chloride gave 3-p-methoxybenzamido-4-phenylbutyric acid ethyl ester (M.P. 102°–104°). A Bischler-Napieralski reaction (boiling with phosphorus oxychloride) gave 3,4-dihydro-1-p-methoxyphenyl-3-isoquinolinylacetic acid ethyl ester. Hydrogenation using a palladium/charcoal (10% w/w) gave cis-1-p-methoxyphenyl-1,2,3,4-tetrahydro-3-isoquinolinylacetic acid ethyl ester.

(b) Reaction of this ester with paraformaldehyde and potassium cyanide gave cis-2-cyanomethyl-1-p-methoxyphenyl-1,2,3,4-tetrahydro-3-isoquinolinyl acetic acid ethyl ester, which was hydrogenated in crude form in the presence of Raney nickel to give cis-2-(2-aminoethyl)-1-p-methoxyphenyl-1,2,3,4-tetrahydro-3-isoquinolinylacetic acid ethyl ester. Cyclization gave (7RS,12aRS)-1,4,5,7,12,12a-hexahydro-7-p-methoxyphenyl-1,4-diazepino[1,7-b]isoquinolin-2 (3H)-one (M.P. 196°–198°).

(c) This aminoketone was alkylated with methyl iodide to give (7RS,12aRS)-1,4,5,7,12,12a-hexahydro-7-p-methoxyphenyl-3-methyl-1,4-diazepino[1,7-b]isoquinolin-2(3H)-one (M.P. 170°–172°).

EXAMPLE 2:
(7RS,12aRS)-3-methyl-1,2,3,4,5,7,12,12a-octahydro-7-phenyl-1,4-diazepino[1,7-b]-isoquinoline In analogous manner to Example 1 (7RS,12aRS)-3-methyl-7-phenyl-1,7,12,12a-tetrahydro-1,4-diazepino-[1,7-b]isoquinolin-2,5(3H,4H)-dione was reacted to yield the title compound (M.P. of maleate from methanol/ether 184°–186°).

The starting material was obtained as follows:

Cis-1-phenyl-1,2,3,4-tetrahydro-3-isoquinolinylacetic acid ethyl ester (M.P. of hydrochloride 219°–222°) was obtained in analogous manner to Example 1 a) using benzoyl chloride instead of p-anisolyl chloride.

Reaction of this ester with bromoacetyl chloride at −10° in the presence of triethylamine gave cis-2-bromoacetyl-1-phenyl-1,2,3,4-tetrahydro-3-isoquinolinylacetic acid ethyl ester (M.P. 107°–109°). Reaction with methylamine in tetrahydrofuran in an autoclave at 50° gave (7RS,12aRS)-1,7,12,12a-3-methyl-7-phenyl-1,7,12,12a-tetrahydro-1,4-diazepino[1,7-b]isoquinolin-2,5(3H,4H)-dione (M.P. 208°–211°).

EXAMPLE 3:
(7aRS,12aRS)-3-ethyl-1,2,3,4,5,7,12,12a-octahydro-7-phenyl-1,4-diazepino[1,7-b]-isoquinoline A solution of 6.0 g of (7RS,12aRS)-3-acetyl-1,2,3,4,5,7,12,12a-octahydro-7-phenyl-1,4-diazepino-[1,7-b]isoquinoline in 100 ml of dioxane was added dropwise into a boiling suspension of 3.14 g of lithium aluminium hydride in 75 ml of dioxane. The reaction mixture was boiled for 1 hour, cooled to 0°, and to this mixture was added carefully dropwise 50 ml of methanol and 50 ml of a saturated solution of sodium sulphate. The resultant precipitate was filtered off. The filtrate was evaporated to dryness to afford the title compound (M.P. of maleate from methanol/ether 156°–158°).

The starting material was obtained as follows:

(a) (7 RS,12aRS)-1,4,5,7,12,12a-hexahydro-7-phenyl-1,4-diazepino[1,7-b]isoquinolin-2(3H)-one [M.P. 232°–234°] was produced in analogous manner to Examples 1 (a) and (b) using benzoyl chloride instead of p-anisolyl chloride. Reduction analogous to Example 1 gave (7 RS,12aRS)-1,2,3,4,5,7,12,12a-octahydro-7-phenyl-1,4-diazepino[1,7-b]isoquinoline (M.P. of maleate 204°–205°).

(b) 3.08 of acetyl chloride diluted with 10 ml of methylene chloride was added dropwise to a solution of 9.9 g (7 RS,12aRS)-1,2,3,4,5,7,12,12a-octahydro-7-phenyl-1,4-diazepino[1,7-b]isoquinoline in 100 ml of methylene chloride. The reaction mixture was stirred for 1 hour, then wasted twice with water, then dried with magnesium sulphate and concentrated to dryness to give (7RS,12aRS)-3-acetyl-1,2,3,4,5,7,12,12a-octahydro-7-phenyl-1,4-diazepino[1,7-b]isoquinoline (M.P. 145°–147°).

EXAMPLE 4:
(7RS,12aRS)-3-methyl-1,2,3,4,5,7,12,12a-octahydro-7-phenyl-1,4-diazepino[1,7-b]-isoquinoline A solution of 6.8 g of (7RS,12aRS)-1,2,3,4,5,7,12,12a-octahydro-7-phenyl-1,4-diazepino[1,7-b]isoquinoline-3-carboxylic acid ethyl ester in toluene was added dropwise slowly into a stirred and boiling mixture of 200 ml of toluene and 21.6 ml of 70% disodium (2-methoxyethoxy)aluminium hydride in benzene. The reaction mixture was refluxed for a further 30 minutes, and cooled to 0°. The complex and remaining reducing agent was decomposed by the slow dropwise addition of 60 ml of a 20% sodium hydroxide solution. The organic phase was separated off, washed with 100 ml of a 20% sodium hydroxide solution, then washed three times with water, then dried with magnesium sulphate, and finally concentrated to dryness to give the title compound (M.P. of maleate from methanol/ether 184°–186°).

The starting material was obtained as follows:

5.4 g of (7RS,12aRS)-1,2,3,4,5,7,12,12a-octahydro-7-phenyl-1,4-diazepino[1,7-b]isoquinoline was dissolved in 75 cc of chloroform and 30 cc of water are added. 4.3 g of chloroformic acid ethyl ester and subsequently a solution of 1.58 g of sodium hydroxide in 30 cc of water were added dropwise at a temperature of 0°–5°. The reaction mixture was stirred for another hour without cooling. The layers were then separated and the organic phase was washed twice with water. After drying with magnesium sulphate and concentration by evaporation of the filtered chloroform solution, the (7RS,12aRS)-1,2,3,4,5,7,12,12a-octahydro-7-phenyl-1,4-diazepino[1,7-b]isoquinoline-3-carboxylic acid ethyl ester was obtained in crude form.

Further compounds of formula I obtained are tabulated below:

| Example | $R_1$ | $R_2$ | $R_3$ | $R_4$ | Configuration | M.P. |
|---|---|---|---|---|---|---|
| Analogous to Example $1^{a)}$, $2^{\beta)}$, $3^{\gamma)}$ and $4^{\delta)}$: | | | | | | |

-continued

| Example | $R_1$ | $R_2$ | $R_3$ | $R_4$ | Configuration | | M.P. |
|---|---|---|---|---|---|---|---|
| 5 | Me | phenyl | 10-OMe | H | cisτ) | m | 159-161° |
| 6 | Me | phenyl | 9-OMe | H | cisτ) | m | 173-175° |
| 7 | Me | p-Cl—phenyl | H | H | cisε) | m | 186-188° |
| 8 | Me | p-Cl—phenyl | H | H | transε) | dh | 198-201° |
| 9 | Me | m-Cl—phenyl | H | H | cisε) | m | 172-174° |
| 10 | Me | o-Cl—phenyl | H | H | cisε) | f | 192-195° |
| 11 | Me | phenyl | 10-Cl | H | cisε) | m | 192-193° |
| 12 | Me | phenyl | H | H | transε) | f | 210-212° |
| 13 | Me | phenyl | 9-Me | H | cisτ) | m | 191-192° |
| 14 | Me | phenyl | 10-Me | H | cisτ) | m | 171-173° |
| 15 | Me | phenyl | 9-MeO | 10-OMe | cisτ) | m | 178-179° |
| 15a | Me | phenyl | 9-Me | 10-OMe | cis | | |
| 16 | Me | benzyl | H | H | cisτ) | m | 149-150° |
| 17 | Me | phenyl | 9-Cl | H | cisε) | m | 200-201° |
| 18 | Me | phenyl | 9-Cl | H | transε) | f | 182-184° |
| 19 | Me | p-Cl—benzyl | H | H | cisε) | b | 85-87° |
| 20 | Me | m-MeO—phenyl | H | H | cisτ) | m | 161-162° |
| 21 | Me | m,p-Di—MeO—phenyl | H | H | cisτ) | m | 174-175° |
| 22 | Me | p-MeO—benzyl | H | H | cisτ) | m | 120-121° |
| 23 | Me | o-MeO—phenyl | H | H | cisτ) | m | 134-137° |

Analogous to Example 2^β), 3γ) and 4^δ):

| 24 | Me | p-MeO-phenyl | H | H | cisτ) | m | 163-164° |

Analogous to Example 1^α) and 2^β):

| 25 | H | phenyl | H | H | cisτ) | m | 204-205° |
| 26 | H | phenyl | 10-OMe | H | cisτ) | b | Oil |
| 27 | H | phenyl | 9-OMe | H | cisτ) | m | 188-190° |
| 28 | H | m-MeO—phenyl | H | H | cisτ) | b | oil |
| 29 | H | p-Cl—phenyl | H | H | cisε) | m | 201-202° |
| 30 | H | phenyl | 10-Cl | H | cisε) | m | 196-197° |
| 31 | H | phenyl | H | H | transε) | f | 176-178° |
| 32 | H | p-MeO—phenyl | H | H | cisτ) | m | 186-188° |
| 33 | H | phenyl | 10-Me | H | cisτ) | m | 209-210° |
| 34 | H | phenyl | 9-Me | H | cisτ) | m | 188-189° |
| 35 | Et | phenyl | H | H | cisτ) | m | 158-160° |

Analogous to Example 1^α) and 3γ):

| 36 | Me | phenyl | H | H | cisτ) | m | 184-186° |

In the Tables
Configuration = Configuration of the hydrogen atoms in the 7 and 12a positions.
b = base; dh = dihydrochloride; f = fumarate; m = maleate; Et = ethyl; Me = methyl.
^α)from the corresponding compound of formula II, wherein X = —CO—; Y = —CH$_2$— and Z =R$_1$
^β)from the corresponding compound of formula II, wherein X = Y = —CO— and Z = R$_1$
^γ)from the corresponding compound of formula II, wherein X = Y = —CH$_2$— and Z = —CHO
^δ)from the corresponding compound of formula II, wherein X = Y = —CH$_2$— and Z is ethoxycarbonyl
^ε)For the preparation of the starting material the substituted cis or trans 1,2,3,4-tetrahydro-3-isoquinolinylacetic acid ethyl ester was produced according to Example 1 a); however, in the last step the reduction of the corresponding substituted 3,4-dihydro-3-isoquinolinylacetic acid ethyl ester was carried out using sodium borohydride in methanol instead of hydrogen gas. The product was a cis/trans mixture which was separated by chromatography on a 50 fold amount of aluminium oxide (activity basicity II) with methylene chloride as eluent.
^τ)The conditions of ε) can also be used.

The following compounds of formula I are also obtained wherein $R_3 = R_4 = $ nPrO; $R_1 = $ CH$_2$.CH(CH$_3$).CH$_2$.CH$_3$; with a trans configuration;

| $R_2$ | |
|---|---|
| a) | 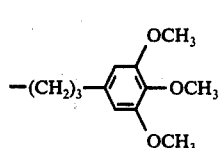 |
| b | 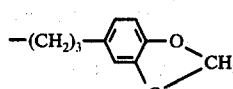 |
| c | 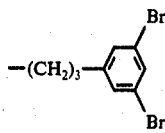 |
| d | 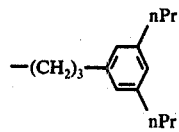 |

The following compounds of formula I, wherein $R_3$ and $R_4 = $ H are also produced,

| | $R_1$ | $R_2$ | Configuration | M.Pt. |
|---|---|---|---|---|
| 37 | CH$_3$ | 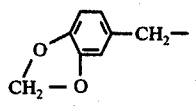 | cis | m 122-5° |
| 38 | CH$_3$ | 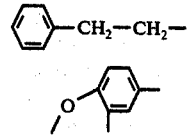 | cis | m 154-5° |
| 39 | CH$_3$ |  | cis | m 180-2° |

-continued

| | $R_1$ | $R_2$ | Configuration | M.Pt. |
|---|---|---|---|---|
| 40 | —(CH$_2$)$_2$—CH$_3$ | 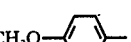 | cis | m 193–5° |
| 41 | —CH—(CH$_3$)$_2$ | 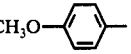 | cis | m 180–2° |
| 42 | CH$_3$ | 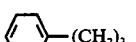 | cis | m 149–150° |
| 43 | CH$_3$ | 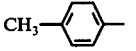 | cis | m 185–6° |
| 44 | CH$_3$ | 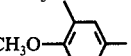 | cis | m 154–6° |
| 45 | CH$_3$ | 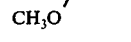 | trans | f 171–3° | m = maleate;
f = fumarate

Examples 37–39 and 42 to 45 are produced in analogous manner to Example 5. Examples 40 and 41 are produced in analogous manner to Example 25.

The compounds of formula I exhibit pharmacological activity. In particular, the compounds exhibit sleep-inducing, sleep-prolonging and sleep-promoting activity as indicated in standard tests in animals.

In one standard test chronically implanted, unrestrained Charles River rats are used. The rats were implanted according to the method of Sayers A.C. and Stille G. [Electroenceph. clin. Neurophysiol. 27, 87–89 (1969)]. For the EEG monopolar connections were made in a Cortex occipitalis, and a right Hippocampus dorsalis. The E.M.G. of the neck muscles was also recorded. The rats were used at least 14 days after the operation.

Thes test substance was administered to the animal in dissolved or suspended form per os. using a stomach tube. The EEG was then observed over the next 3 hours. The animals were kept in a box which they also lived outside the observation period. During this time the animals were under constant lighting conditions and insulated against noise and electrical disturbances. Food and water were available ad libitum. The increase in the sleep phase and decrease in the wake phase was observed by means of the E.E.G.

In this test the compounds are administered p.o. at a dose of from about 0.1 to about 40 mg/kg animal body weight.

Additionally the compounds exhibit locomotor-depressant activity in the well known light box test.

In this test the compounds are administered p.o. at a dose of from about 0.1 to about 40 mg/kg animal body weight.

For the above-mentioned use the dosage will, of course, vary depending on the compound employed, mode of administration and therapy desired. However, in general, satisfactory results are obtained when administered at a daily dosage of from 0.1 mg to about 40 mg per kg animal body weight, conveniently given in single doses once a day or in sustained release form shortly, e.g. ½ hour, before retiring to bed. For the larger mammal, the total daily dosage for oral usage is in the range from about 1 to about 400 mg, preferably 1 to 200 mg.

The compounds of Examples 1 and 2 are the most interesting compounds.

Furthermore the compounds exhibit anti-aggresive activity, e.g. for the treatment of psychopaths and imbeciles as indicated in standard tests. In one standard test the compounds inhibit isolation-induced aggressive behaviour according to the method of H.C.Y. Yen et al [J. Pharmacol. exp. Ther. 122, 85A [1958]].

The compounds are administered p.o. at a dose of from about 2 to about 30 mg/kg animal body weight. The compounds exhibit significant activity in the well known climbing test at higher doses than those at which they are significantly effective in the anti-aggression test.

For the above mentioned use the dosage will, of course, vary depending on the compound employed, mode of administration and therapy desired. However, in general, satisfactory results are obtained when administered at a daily dosage of from 0.05 mg to about 30 mg per kg animal body weight, conveniently given in divided doses 2 to 4 times a day or in sustained release form. For the larger mammal, the total daily dosage is in the range from about 20 to about 300 mg, and dosage forms suitable for oral administration comprise from about 5 mg to about 150 mg, preferably 5 to 100 mg of the compounds admixed with a solid or liquid pharmaceutical carrier or diluent.

The compounds of Examples 1, 2 and 19 are the most interesting compounds.

The compounds are furthermore useful as inhibitors of blood platelet aggregation, e.g. for the treatment and prophylaxis of thromboembolic diseases, e.g. thrombosis, as indicated in standard tests. For example, the compounds inhibit collagen-induced blood platelet aggregation using rabbit plasma, in vitro at from about 5 to about 50 μM and ex vivo at from about 10 to about 50 mg/kg.

For the above-mentioned use the dosage will, of course, vary depending on the compound employed, mode of administration and therapy desired. However, in general, satisfactory results are obtained when administered at a daily dosage of from 0.1 mg to about 50 mg per kg animal body weight, conveniently given in divided doses 2 to 4 times a day or in sustained release form. For the larger mammal, the total daily dosage is in the range from about 10 to about 500 mg, and dosage forms suitable for oral administration comprise from about 2 mg to about 250 mg of the compounds admixed with a solid or liquid pharmaceutical carrier or diluent.

The compound of Example 43 exhibits particularly interesting sleep-promoting/inducing activity accompanied by a significant anti-cholinergic effect.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

Preferably $R_1$ is ethyl or especially methyl. Preferably $R_2$ is phenyl or benzyl, conveniently preferably para-substituted by halogen, e.g. chlorine, or methoxy.

Preferably the 7 and 12a hydrogen atoms are cis.

We claim:

1. A compound of formula I,

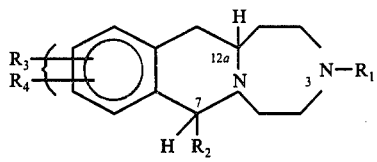

wherein $R_1$ is hydrogen or alkyl of 1 to 5 carbon atoms, $R_2$ is a group

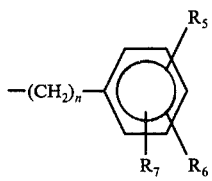

wherein n is a whole number from 0 to 3, $R_5$ and $R_6$, independently, are hydrogen, alkyl of 1 to 4 carbon atoms, alkoxy of 1 to 4 carbon atoms, halogen of atomic number from 9 to 35, or together are 3,4-methylenedioxy, $R_7$ is hydrogen, or when both $R_5$ and $R_6$ are alkoxy of 1 to 4 carbon atoms also may be alkoxy of 1 to 4 carbon atoms, $R_3$ is hydrogen, alkyl of 1 to 4 carbon atoms, alkoxy of 1 to 4 carbon atoms, or halogen of atomic number from 9 to 35, and $R_4$ is hydrogen or alkoxy of 1 to 4 carbon atoms, in free base form or in pharmaceutically acceptable acid addition salt form.

2. A compound of formula I, as defined in claim 1.

3. A compound of claim 1 having the formula

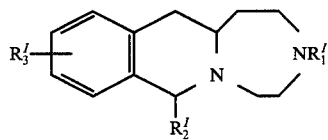

wherein $R_1{}^I$ signifies alkyl, $R_2{}^I$ signifies phenyl or phenyl substituted by one or two substituents of the series halogen, alkyl or alkoxy, and $R_3{}^I$ signifies hydrogn, halogen or alkoxy, as defined in claim 1.

4. A compound of claim 3, wherein $R_1{}^I$ is methyl, $R_2{}^I$ is phenyl, p-methoxyphenyl or o-, m- or p-chlorophenyl, and $R_3{}^I$ is hydrogen or chlorine in the 10 position.

5. A pharmaceutical composition for use in treating aggression or inducing or promoting sleep comprising an effective amount of a compound according to claim 1 in association with a pharmaceutical carrier or diluent.

6. A method of treating aggression in animals which comprises administering to an animal in need of such treatment a therapeutically effective amount of a compound of claim 1.

7. A method of inducing or promoting sleep in animals which comprises administering to an animal in need of such treatment a therapeutically effective amount of a compound of claim 1.

8. The compound of claim 1, wherein the configuration of the hydrogen atoms in the positions 7 and 12a is cis.

9. A compound of claim 8, wherein $R_1$ is methyl.

10. The compound of claim 9, wherein $R_2$, $R_3$ and $R_4$ are respectively phenyl, 10-OMe and H.

11. The compound of claim 9, wherein $R_2$, $R_3$ and $R_4$ are respectively phenyl, 9-OMe and H.

12. The compound of claim 9, wherein $R_2$, $R_3$ and $R_4$ are respectively p-Cl-phenyl, H and H.

13. The compound of claim 9, wherein $R_2$, $R_3$ and $R_4$ are respectively m-Cl-phenyl, H and H.

14. The compound of claim 9, wherein $R_2$, $R_3$ and $R_4$ are respectively o-Cl-phenyl, H and H.

15. The compound of claim 9, wherein $R_2$, $R_3$ and $R_4$ are respectively phenyl, 10-Cl and H.

16. The compound of claim 9, wherein $R_2$, $R_3$ and $R_4$ are respectively phenyl, 9-Me and H.

17. The compound of claim 9, wherein $R_2$, $R_3$ and $R_4$ are respectively phenyl, 10-Me and H.

18. The compound of claim 9, wherein $R_2$, $R_3$ and $R_4$ are respectively benzyl, H and H.

19. The compound of claim 9, wherein $R_2$, $R_3$ and $R_4$ are respectively phenyl, 9-Cl and H.

20. The compound of claim 9, wherein $R_2$, $R_3$ and $R_4$ are respectively p-Cl-benzyl, H and H.

21. The compound of claim 9, wherein $R_2$, $R_3$ and $R_4$ are respectively m-MeO-phenyl, H and H.

22. The compound of claim 9, wherein $R_2$, $R_3$ and $R_4$ are respectively m,p-Di-MeO-phenyl, H and H.

23. The compound of claim 9, wherein $R_2$, $R_3$ and $R_4$ are respectively p-MeO-benzyl, H and H.

24. The compound of claim 9, wherein $R_2$, $R_3$ and $R_4$ are respectively o-MeO-phenyl, H and H.

25. The compound of claim 9, wherein $R_2$, $R_3$ and $R_4$ are respectively p-MeO-phenyl, H and H.

26. A compound of claim 8, wherein $R_1$ is hydrogen.

27. The compound of claim 26, wherein $R_2$, $R_3$ and $R_4$ are respectively phenyl, H and H.

28. The compound of claim 26, wherein $R_2$, $R_3$ and $R_4$ are respectively phenyl, 10-Ome and H.

29. The compound of claim 26, wherein $R_2$, $R_3$ and $R_4$ are respectively phenyl, 9-Ome and H.

30. The compound of claim 26, wherein $R_2$, $R_3$ and $R_4$ are respectively m-MeO-phenyl, H and H.

31. The compound of claim 26, wherein $R_2$, $R_3$ and $R_4$ are respectively p-Cl-phenyl, H and H.

32. The compound of claim 26, wherein $R_2$, $R_3$ and $R_4$ are respectively phenyl, 10-Cl and H.

33. The compound of claim 26, wherein $R_2$, $R_3$ and $R_4$ are respectively p-MeO-phenyl, H and H.

34. The compound of claim 26, wherein $R_2$, $R_3$ and $R_4$ are respectively phenyl, 10-Me and H.

35. The compound of claim 26, wherein $R_2$, $R_3$ and $R_4$ are respectively phenyl, 9-Me and H.

36. The compound of claim 8, wherein $R_1$, $R_2$, $R_3$ and $R_4$ are respectively Et, phenyl, H and H.

37. The compound of claim 8, wherein $R_1$, $R_2$, $R_3$ and $R_4$ are respectively Me, phenyl, H and H.

38. A compound of claim 1, wherein the configuration of the hydrogen atoms in positions 7 and 12a is trans.

39. The compound of claim 38, wherein $R_1$, $R_2$, $R_3$ and $R_4$ are respectively Me, p-Cl-phenyl, H and H.

40. The compound of claim 38, wherein $R_1$, $R_2$, $R_3$ and $R_4$ are respectively Me, phenyl, H and H.

41. The compound of claim 38, wherein $R_1$, $R_2$, $R_3$ and $R_4$ are respectively Me, phenyl, 9-Cl and H.

42. The compound of claim 38, wherein $R_1$, $R_2$, $R_3$ and $R_4$ are respectively H, phenyl, H and H.

43. The compound of claim 9, wherein $R_2$, $R_3$ and $R_4$ are respectively phenyl, 9-MeO and 10-MeO.

44. The compound of claim 9, wherein $R_2$, $R_3$ and $R_4$ are respectively phenyl, 9-Me and 10-MeO.

45. A method of inducing or promoting sleep in animals which comprises administering to an animal in need of such treatment or therapeutically effective amount of a compound of claim 25.

46. A method of inhibiting blood platelet aggregation in animals which comprises administering to an animal in need of such treatment a therapeutically effective amount of a compound of claim 1.

47. A compound of claim 9, wherein $R_3$ and $R_4$ are each hydrogen.

48. The compound of claim 47, wherein $R_2$ is

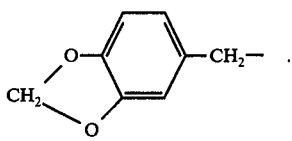

49. The compound of claim 47, wherein $R_2$ is

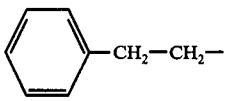

50. The compound of claim 47, wherein $R_2$ is

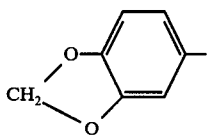

51. The compound of claim 8, wherein $R_1$, $R_2$, $R_3$ and $R_4$ are respectively

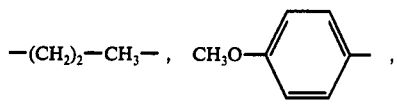

H and H.

52. The compound of claim 8, wherein $R_1$, $R_2$, $R_3$ and $R_4$ are respectively

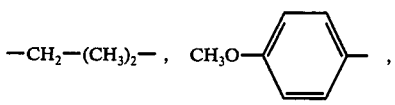

H and H.

53. The compound of claim 47, wherein $R_2$ is

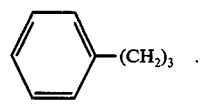

54. The compound of claim 47, wherein $R_2$ is

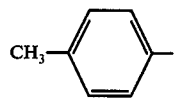

55. The compound of claim 47, wherein $R_2$ is

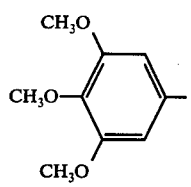

56. A compound of claim 38, wherein $R_3$ and $R_4$ are each hydrogen.

57. The compound of claim 56, wherein $R_1$ is methyl and $R_2$ is

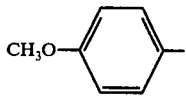

* * * * *